US012564629B2

(12) United States Patent
Bijlsma et al.

(10) Patent No.: US 12,564,629 B2
(45) Date of Patent: Mar. 3, 2026

(54) VACCINE TO PROTECT AGAINST MYCOPLASMA HYOPNEUMONIAE

(71) Applicant: Vaxinano SAS, Loos (FR)

(72) Inventors: Johanna Jacoba Elisabeth Bijlsma, Boxmeer (NL); Maarten Hendrik Witvliet, Boxmeer (NL); Didier Betbeder, Loos (FR)

(73) Assignee: Vaxinano SAS, Loos (FR)

( * ) Notice: Subject to any disclaimer, the term of this patent is extended or adjusted under 35 U.S.C. 154(b) by 481 days.

(21) Appl. No.: 17/917,987

(22) PCT Filed: Apr. 19, 2021

(86) PCT No.: PCT/EP2021/060013
§ 371 (c)(1),
(2) Date: Oct. 10, 2022

(87) PCT Pub. No.: WO2021/213948
PCT Pub. Date: Oct. 28, 2021

(65) Prior Publication Data
US 2023/0145957 A1     May 11, 2023

(30) Foreign Application Priority Data

Apr. 20, 2020    (EP) ..................................... 20170440

(51) Int. Cl.

| | |
|---|---|
| *A61K 39/02* | (2006.01) |
| *A61K 39/295* | (2006.01) |
| *A61P 31/04* | (2006.01) |
| *A61K 39/00* | (2006.01) |
| *B82Y 5/00* | (2011.01) |

(52) U.S. Cl.
CPC ........ *A61K 39/295* (2013.01); *A61K 39/0241* (2013.01); *A61P 31/04* (2018.01); *A61K 2039/522* (2013.01); *A61K 2039/5254* (2013.01); *A61K 2039/545* (2013.01); *A61K 2039/552* (2013.01); *A61K 2039/55555* (2013.01); *B82Y 5/00* (2013.01)

(58) Field of Classification Search
None
See application file for complete search history.

(56) References Cited

U.S. PATENT DOCUMENTS

| | | | |
|---|---|---|---|
| 8,828,929 | B2 | 9/2014 | Matsui |
| 2009/0304737 | A1 | 12/2009 | Drexler et al. |

FOREIGN PATENT DOCUMENTS

| | | |
|---|---|---|
| EP | 2708237 A1 | 3/2014 |
| WO | 2014041427 A1 | 3/2014 |
| WO | 2017162741 A1 | 9/2017 |
| WO | 2018104762 A1 | 6/2018 |
| WO | WO 2020018429 A1 | 1/2020 |

OTHER PUBLICATIONS

Paillard Archibald et al., Positively-Charged, Porous, Polysaccharide Nanoparticles Loaded with Anionic Molecules Behave as 'Stealth' Cationic Nanocarriers, Pharmaceutical Research, 2010, 126-133, 27(1).

Dimier-Poisson et al., 2015, "Porous nanoparticles as delivery system of complex antigens for an effective vaccine against acute and chronic Toxoplasma gondii infection," Biomaterials, 50:164-175.

Matthijs et al., 2019, "Systems Immunology Characterization of Novel Vaccine Formulations for Mycoplasma hyopneumoniae Bacterins," Front Immunol., 10:1087 (19 pages).

Karkishchenko, V.N. et al., Pharmacological bases of therapy, Thesaurus: Handbook for doctors and students, Third edition, 7-8, 2018 (English Translation).

*Primary Examiner* — Jennifer E Graser

(74) *Attorney, Agent, or Firm* — TraskBritt

(57) ABSTRACT

A vaccine comprising nanoparticles in association with a *Mycoplasma hyopneumoniae* bacterin, wherein the nanoparticles comprise a cationic polysaccharide and an anionic phospholipid.

14 Claims, No Drawings

VACCINE TO PROTECT AGAINST MYCOPLASMA HYOPNEUMONIAE

CROSS-REFERENCE TO RELATED APPLICATIONS

This application is a National Stage application of International Patent Application No. PCT/EP2021/060013, filed Apr. 19, 2021, which claims priority to European Patent Application No. EP 20170440.0, filed Apr. 20, 2020.

FIELD OF THE INVENTION

The present invention is directed to a vaccine comprising nanoparticles in association with a *Mycoplasma hyopneumoniae* bacterin as well as the use of this vaccine for the prophylaxis of an infection in pigs.

BACKGROUND OF THE INVENTION

*Mycoplasma hyopneumoniae* (in the following also referred to as Mhyo) is a cell wall deficient bacterium and the causative agent of porcine enzootic pneumonia, a contagious and chronic disease in pigs. Mhyo infects the respiratory tract of pigs and grows on the trachea, bronchi and bronchioles. It attaches to and eventually kills the cilia of epithelial lung cells, resulting in lung lesions and secondary infections, such as infections by other *Mycoplasma* species, e.g. *Mycoplasma hyorhinis* and *Mycoplasma flocculare*, as well as infections with PRRSV (Porcine Reproductive and Respiratory Syndrome Virus) and PCV2 (Porcine Virus Type 2).

The disease is transmitted from pig to pig by airborne Mhyo pathogen expelled from the lungs of infected pigs.

In particular, the infection with Mhyo results in reduced weight gain, worse feed conversion and thus leads to significant economic loss in commercial pig farms.

Since the Mhyo bacterium lacks a cell wall, most common antibiotics are ineffective, as they focus on the cell wall synthesis.

Vaccines for use against the Mhyo pathogen are known and are commercially available, e.g. RespiSure® (Zoetis), Ingelvac® *M. hyo*, and MycoFLEX® (Boehringer Ingelheim), Hyoresp® (Merial), Stellamune® *Mycoplasma* (Elanco Animal Health), Fostera® PCV MH (Zoetis) and M+Pac® and Porcilis® Mhyo (both available from MSD Animal Health).

These vaccines all contain classical adjuvants, containing non-self compounds as adjuvants such as mineral and vegetable oils, non natural polymers and aluminium hydroxide, to enhance the immune response and optionally also to stabilize the Mhyo antigen. The non-self compounds enhance the immune response but may also give rise to unwanted site effects. In particular pigs are very sensitive for excipients such as mineral oils, alum particles and other non-self compounds. It was an object of the present invention to provide a vaccine that is effective but does not induce site effects typically associated with classical adjuvants.

In addition, it was an object of the present invention to provide a vaccine for use in the prophylaxis of a *Mycoplasma hyopneumoniae* infection that is convenient, safe and efficacious.

Additionally, the commercial vaccines are commonly administered as a two-shot regime by a prime vaccination followed by a boost vaccination within 2 or 3 weeks from the first administration to ensure successful immunization. However, such a two-shot application is disadvantageous in terms of efficiency and cost.

Thus, it was a further object to provide a vaccine that is effective in a one-shot regime.

Furthermore, combination vaccines are cumbersome to develop, as safety and stability of all vaccine-components must be ensured, and the development of combination vaccines is not straightforward. In particular the combination of a live attenuated vaccine and a bacterin vaccine is detrimental for stability and it is difficult to select excipients that stabilize both types of antigens.

Thus, it was a further object to provide a combination vaccine that is safe to use and/or stable.

SUMMARY OF THE INVENTION

These objects have surprisingly been solved by the following aspects of the invention:

A composition according to the present invention comprises nanoparticles in association with a *Mycoplasma hyopneumoniae* bacterin, wherein the nanoparticles comprise a cationic polysaccharide and an anionic phospholipid.

It has surprisingly been found that a vaccine comprising a Mhyo bacterin and the above-mentioned nanoparticles, containing a polysaccharide (a common dietary compound) and phospholipids (subject's own compound, i.e. a self-compound) provides a stable and effective vaccine for the prophylaxis of an infection with *Mycoplasma hyopneumoniae*, whilst not inducing unwanted site effects.

Thus, the present invention also relates to the vaccine for use in the prophylaxis of an infection with *Mycoplasma hyopneumoniae* in pigs. In the following, this vaccine may also be referred to as the vaccine according to the present invention.

The present invention also relates to a kit of parts comprising a first vaccine, a second vaccine and a leaflet, wherein the first vaccine is a vaccine according to the present invention and the second vaccine comprises live attenuated porcine reproductive and respiratory syndrome virus (PRRSV).

In another aspect, the present invention relates to a method for the prophylaxis of an infection with *Mycoplasma hyopneumoniae* in pigs comprising administering an effective amount of the vaccine.

In yet another aspect, the present invention relates to the use of the vaccine of the present invention for the manufacture of a medicament for the prophylaxis of an infection with *Mycoplasma hyopneumoniae* in pigs.

In yet another aspect, the present invention relates to a combination vaccine comprising in a vial a mixture of a first vaccine and a second vaccine, wherein the first vaccine is a vaccine according to the present invention and the second vaccine comprises live attenuated porcine reproductive and respiratory syndrome virus (PRRSV). The combination vaccine may be a so-called RTU (ready-to-use) vaccine, thus delivered to an end user in a mixed form as produced by the manufacturer, or may for example be a vaccine that is mixed just prior to administration to a subject animal, for example by dissolving the PRRS virus in the Mhyo vaccine.

DETAILED DESCRIPTION

The following definitions are relevant in connection with the embodiments of the present invention.

The term "vaccine" relates to a pharmaceutical composition. The composition is able to induce protective immunity in an animal against a pathogenic microorganism (a "pathogen"), i.e. to induce an effective prophylactic treatment against an infection with the pathogen and/or a disorder or disease that is the result of this infection.

Antigens in general relate to any substance that induces a specific immune response in a host animal and may comprise a whole organism, killed, attenuated or live, a subunit or portion of an organism, a recombinant vector containing a polynucleotide encoding an immunogen, a protein, a polypeptide, a peptide, an epitope, a hapten, or any combination thereof. Bacterins are specific antigens. The term "bacterin" refers to a suspension of killed bacteria, e.g. obtained by concentration of a bacterial culture that is subsequently inactivated with a chemical agent such as binary ethylenimine (BEI), chlorocresol, formaline, or for example by UV light or other types of inactivation not directed at lysis of the cells. In contrast to a bacterin, a lysate is an antigen wherein the inactivated bacterium is expressly treated in a cell lysis or disruption process such as e.g. freeze-thaw cycles, sonication, French pressing, bead beating etc.

"Nanoparticles" are particles having a particle size in the nm region, i.e. a mean volume particle diameter ($D_{50}$) between 1 and 1000 nm. In an embodiment, the nanoparticles have a mean volume particle diameter ($D_{50}$) of from 1 to 500 nm. For example, the mean volume particle diameter is between 10 and 400 nm, such as between 20 and 300 nm and between 30 and 200 nm. Typically, the mean volume particle diameter is between 35 and 150 nm. The mean volume particle diameter can be determined by laser diffraction. In a preferred embodiment the particle diameter is measured by dynamic light scattering using a Malvern Autosizer™ 4700 (Malvern Instruments S.A., UK). It is preferred that the measurement is conducted with a 488 nm laser beam at a fixed angle of 90°. An aqueous solution of 15 mMol NaCl is preferably used as dispersant, wherein the nanoparticles are concentrated at 0.5 mg/ml. Measurements are preferably carried out in triplicate.

The term "zeta potential" refers to the electrical charge between the dispersion medium and the stationary layer of the dispersed particle. The zeta potential is therefore a function of the surface charge of the particle, any adsorbed layer at the interface and the nature and composition of the surrounding suspension medium. In a preferred embodiment, the zeta potential is determined by photon correlation spectroscopy using a zetasizer nano ZS (Malvern Instruments, France). It is preferred that the measurement is conducted in water as medium. Measurements are preferably carried out in triplicate.

The term "effective prophylactic treatment" or "prophylaxis" of an infection is to be understood to encompass the prevention, amelioration or mitigation of a post treatment infection or a disease or disorder arising from that post treatment infection.

The term "one-shot" or "single dose" administration of a vaccine for use in the prophylaxis relates to a vaccination that does not require a second or "boost"-vaccination and is still effective in providing protective immunity. It is noted that the term does not exclude that the single dose is administered as two or more separate doses administered concurrently.

The meaning of the term "comprising" is to be interpreted as encompassing all the specifically mentioned features as well as optional, additional, unspecified ones, whereas the term "consisting of" only includes those features as specified. Therefore, "comprising" includes as a limiting case the composition specified by "consisting of".

The term "pig" as used herein, refers to piglets, swine, pigs, porcine, sows, gilts, barrows, boars, i.e. all members of the Suidae family.

The term "wt.-%" refers to the weight amount of a specific component based on the total weight of vaccine, unless denoted otherwise.

Preferred embodiments according to the invention are defined hereinafter. The preferred embodiments are preferred alone or in combination. Further, it is to be understood that the following preferred embodiments refer to all aspects of the present invention, i.e. the vaccine, the vaccine for use, the kit of parts, the method of treating, the use for manufacture of a medicament and the combination vaccine.

In an embodiment, the invention relates to a vaccine comprising nanoparticles in association with a *Mycoplasma hyopneumoniae* bacterin, wherein the nanoparticles comprise a cationic polysaccharide and an anionic phospholipid.

The nanoparticles of the present invention are known and methods for obtaining said particles are described i.a. in Paillard et al., Pharm. Res. 2010, vol. 27, p. 126-133, WO 2014/041427 and WO 2018/104762, as well as in the references therein.

In a preferred embodiment, the cationic polysaccharide can be prepared by dissolving the respective polysaccharide (e.g. maltodextrin in a 2 N aqueous sodium hydroxide solution) and adding a crosslinking agent (e.g. epichlorohydrin), followed by addition of a cationic ligand (e.g. glycidyl-trimethylammonium chloride; hydroxycholine). The pH value can then be neutralized, preferably with acetic acid, and the mixture sheared, preferably under pressure to obtain cationic polysaccharide nanoparticles.

The obtained cationic polysaccharide is subsequently loaded with anionic phospholipids, preferably by mixing the cationic biopolymer and anionic phospholipids (e.g. dipalmitoyl-phosphatidyl glycerol) in a suitable solvent (e.g. ethanol for e.g. approximately 1 hour).

In an embodiment, the cationic polysaccharide is a porous, cationic polysaccharide.

The nanoparticles can be porous nanoparticles, i.e. having voids in the "bulk" of the particles such that liquid or air can pass into the particles. The cationic polysaccharide thus may be porous so that the anionic phospholipid can fill the pores and the anionic phospholipid is present at least partly in the core of the nanoparticles.

Typically, the (porous) particles have a BET (specific surface area) of at least 0.1 $m^2$/g, at least 0.5 $m^2$/g, 5 $m^2$/g, at least 10 $m^2$/g, or at least 20 $m^2$/g. Preferably, the BET of the nanoparticles is at least 5 $m^2$/g. The determination of the specific surface area is carried out by placing the sample in a nitrogen/helium atmosphere at different pressures. Cooling the sample causes condensation of the nitrogen molecules on the surface of the particles. The condensed nitrogen quantity is determined by the change of the thermal conductivity of the nitrogen/helium mixture and the surface area of the sample is determined using the area requirement of nitrogen. The specific surface area is calculated using this value and the sample weight. The specific surface area can be obtained by using BET sorptometer, such as a Monosorb™, Fa. Quantachrome, following DIN ISO 9277 (published in January 2014).

In an embodiment, the nanoparticles comprise the cationic polysaccharide and the anionic phospholipid in a weight ratio of 40:1 to 1:20, of 20:1 to 1:10, or of 10:1 to 1:3. In a preferred embodiment, the nanoparticles comprise the cationic polysaccharide and the anionic phospholipid in a weight ratio of 10:1 to 1:3.

In an embodiment, the nanoparticles have a zeta potential of between 0 and 70 mV, of between 5 and 65 mV or of between 10 and 50 mV. It is preferred that the nanoparticles have a zeta potential of between 10 and 50 mV.

The nanoparticles have an outside portion, i.e. a surface, and an inside portion, i.e. a core. In a particular embodiment it can be inferred i.a. from the zeta potential of the nanoparticles that the outside portion is essentially free of the anionic phospholipid. Thus, the outside portion essentially consists of the cationic polysaccharide and the core contains the anionic phospholipid. In a preferred embodiment, the cationic polysaccharide is porous. In this embodiment the anionic phospholipids preferably fill the pores. Thus, in a preferred embodiment, the anionic phospholipid is present inside of the nanoparticles, i.e. the core. In a preferred embodiment the nanoparticles form a core, wherein the anionic phospholipid is present within the core. In an embodiment, the nanoparticles do not comprise a phospholipidic layer surrounding the core. A phospholipidic layer is a layer comprising phospholipids.

The Mhyo bacterin is commercially available and methods for obtaining the bacterin are known to the skilled person, e.g. by cultivating Mhyo cells and subsequent inactivation of the cells.

In an embodiment, the vaccine has a weight ratio of nanoparticles to Mhyo bacterin of from 1:10 to 10:1, of from 1:5 to 5:1 or of from 1:2 to 2:1. In a preferred embodiment, the weight ratio of nanoparticles to Mhyo bacterin is from 1:1 to 1:3, such as for example 1:1.

The Mhyo bacterin and the nanoparticles are in association, i.e. they form a composition wherein the bacterin is bonded to the particles by intermolecular forces such as VanderWaals forces and electrostatic forces. It is believed that the Mhyo bacterin is associated to the outside of the nanoparticle. In an embodiment, the nanoparticles being associated with the Mhyo bacterin have an observed $D_{50}$ value (using a laser diffraction method) of between 200 and 1500 nm, or between 300 and 1200 nm, or between 400 and 1100 nm (the observed value depends largely on the measurement method).

It is preferred that the cationic polysaccharide is obtainable from the polysaccharides selected from starch, dextran and maltodextrin. It is more preferred that the cationic polysaccharide core is a crosslinked polymer obtainable by reacting a polysaccharide selected from starch, dextran and maltodextrin and a ligand chosen from primary-, secondary- and tertiary amines and quaternary ammonium salts. Crosslinking agents are known to the skilled person and a preferred crosslinking agent is epichlorohydrin (1-chloro-2,3-epoxypropane).

In an embodiment, the anionic phospholipid is selected from diacylphosphatidyl glycerol, diacylphosphatidyl serine and diacylphosphatidyl inositol, wherein the acyl in each case may be derived from a carboxylic acid. In a preferred embodiment, the anionic phospholipid is dipalmitoyl-phosphatidyl glycerol (DPPG).

The cationic polysaccharide core can be loaded with the anionic phospholipid by mixing the polysaccharide core and the anionic phospholipid. It is to be understood that the term "loaded" refers to a mixture of anionic phospholipid and the cationic polysaccharide.

In an embodiment, the cationic polysaccharide is a cationic polymaltodextrin, obtainable by reacting crosslinked maltodextrin with glycidyl-trimethylammonium.

In an embodiment, the vaccine comprises a pharmaceutically acceptable solvent, thereby providing the vaccine as a so called ready-to-use vaccine. Preferably, the solvent comprises water and the bacterin is diluted in such a way that it still retains its effectiveness. In a preferred embodiment, the solvent comprises an aqueous saline solution and/or a phosphate buffered aqueous saline solution (PBS). In another embodiment, the vaccine may be provided as a lyophilizate that is mixed with the pharmaceutically acceptable solvent prior to administration.

In an embodiment, the vaccine is essentially free of classical adjuvants such as oil and/or aluminium hydroxide, and/or saponins and/or carbopol.

"Essentially free" refers to a concentration below 0.1% (v/v) based on the total composition of the vaccine.

Adjuvants in general can be classified according to the immunological events they induce. The first class, comprising i.a. ISCOM's (immunostimulating complexes), saponins (or fractions and derivatives thereof such as Quil A), aluminium hydroxide, liposomes, cochleates, polylactic/glycolic acid, facilitates the antigen uptake, transport and presentation by APC's (antigen presenting cells). The second class, comprising i.a. oil emulsions, gels, polymer microspheres, non-ionic block copolymers and most probably also aluminum hydroxide, provide for a depot effect. The third class, comprising i.a. CpG-rich motifs, monophosphoryl lipid A, mycobacteria (muramyl dipeptide), yeast extracts, cholera toxin, is based on the recognition of conserved microbial structures, so-called pathogen associated microbial patterns (PAMPs), defined as signal 0. The fourth class, comprising i.a. oil emulsion, surface active agents, aluminium hydroxide, hypoxia, is based on stimulating the distinguishing capacity of the immune system between dangerous and harmless (which need not be the same as self and non-self). The fifth class, comprising i.a. cytokines, is based on the upregulation of costimulatory molecules, signal 2, on APCs. An adjuvant helps in providing an adequate immune response. Although the present nanoparticles cannot be clearly identified to belong to one of these classes, it appears that in some particular constellations an adjuvanting effect may still be obtained.

The vaccine may optionally contain auxiliary substances, such as wetting agents, pH buffering agents, viscosity enhancing additives and preservatives. Suitable auxiliary substances are for example disclosed in "Pharmaceutical Preformulation and Formulation", by Mark Gibson, $2^{nd}$ edition.

It is to be understood that the vaccine contains the Mhyo bacterin in an immunologically effective amount. Such an amount can be easily established based on common knowledge and could for example be the amount of Mhyo bacterin as present in the commercial product Porclis Mhyo ID ONCE (MSD Animal Health), or any of the other bacterin products available in the market.

In an embodiment, the vaccine is administered to a target animal in a volume of between 0.1 and 3 ml per dose, preferably between 0.2 and 2 ml per dose. In an embodiment, the vaccine contains 2 μg to 10 mg, 10 μg to 5 mg, 20 μg to 2000 μg or 200 μg to 2000 μg of nanoparticles per dose of vaccine. Typically, the vaccine contains between 1 and 5 mg of nanoparticles per dose of vaccine.

In an embodiment, the vaccine is used for the prophylaxis of an infection with *Mycoplasma hyopneumoniae* in pigs.

In an embodiment, the vaccine for use is administered between week 1 and week 5, for example between week 2 and week 4 of the life of a pig (after birth). In another embodiment, the vaccine for use is administered between week 1 and week 5 of life as a one-shot regime.

In another embodiment, the vaccine is administered systemically. In contrast to a local administration (such as for example intranasally or intragastrically), systemic administration means that the vaccine is delivered in the circulatory system of the subject and thus inherently affects its whole body. Examples of systemic administration include intramuscular (IM), intravenous (IV), intradermal (ID), transdermal (TD) and sub-cutaneous (SC).

In an embodiment, the vaccine is administered intradermally. It is preferred that the vaccine is administered by needle-free injection by using an IDAL™ (intradermal application of liquids) injection system. DAL is a pressure-based application system (from MSD Animal Health).

In an embodiment, the vaccine for use is administered as a single dose. Thus, the vaccine is administered as a one-shot administration in contrast to being administered multiple times (e.g. a two-shot application comprising a prime- and a boost vaccination).

In a preferred embodiment, the vaccine for use is administered to a target animal intradermally as a single dose.

Typically, the vaccine is used for the reduction of lung lesions due to the infection with *Mycoplasma hyopneumoniae*. It was found that the lung lesions are reduced by 10 to 100%, and even by 50 to 100% compared to mock-vaccinated control pigs.

A lung lesion score (LLS) using a common scoring system, may be reduced by 10 to 100%, typically by 50 to 100% compared to untreated control pigs.

The LLS is measured after three weeks of challenge, as described in more detail in Example 1. The reduction of the lung lesions and the LLS refers to the comparison of pigs treated with the vaccine of the present invention in comparison to non-treated pigs. The LLS is a helpful indicator regarding the effectiveness of immunization by the vaccine. The LLS can be determined by measuring the percentage of lung lesions and transforming this into a Goodwin & Whittlestone score (Goodwin et al. Veterinary Record, "The detection of enzootic pneumonia in pig herds. I. Eight years general experience with a pilot control scheme"), resulting in the LLS.

In an embodiment, the present invention relates to a kit of parts comprising a first vaccine, a second vaccine and a leaflet, wherein the first vaccine is a vaccine according to the present invention and the second vaccine comprises live attenuated porcine reproductive and respiratory syndrome virus (PRRSV). The leaflet contains instruction for use. The kit of parts may further comprise a needle and/or syringe.

A live attenuated pathogen is a viable, replication-competent form of the pathogen having reduced virulence. The process of attenuation takes an infectious pathogen and alters it so that it becomes harmless or less virulent, by e.g. multiple passages of the pathogen through cell systems or by genetically modifying the pathogen.

In an embodiment, the present invention relates to a combination vaccine comprising a mixture of a first vaccine and a second vaccine, wherein the first vaccine is a vaccine according to the present invention and the second vaccine comprises live attenuated porcine reproductive and respiratory syndrome virus (PRRSV).

Alternatively to being administered simultaneously, the first and second vaccine may also be provided as associated non-mixed vaccines for concurrent administration. Thus, the vaccines are not mixed before administration but are administered separately to the pig within a time frame of 1 hour, preferably within 30 min, 25 min, 20 min, 15 min, 10 min, 9 min, 8 min, 7 min, 6 min, 5 min, 4 min, 3 min, 2 min or 1 min.

However, a combination of two vaccines is generally advantageous to minimize the amounts of injections admin istered to each pig and additionally increases efficiency. However, stability problems are common when two or more vaccines are admixed, as each vaccine may require different excipients, thus leading to instability, decreased activity and/or degradation of one of the vaccines. Surprisingly, the stability of live attenuated PRRSV was increased in the presence of the nanoparticles of the present invention.

In an embodiment, the combination vaccine according to the invention is used for the prophylaxis of a Mhyo infection and the prophylaxis of a PRRSV infection.

In an embodiment, the present invention relates to a vial comprising the vaccine according to the present invention or the combination vaccine according to the present invention. It is preferred that the vials are PET vials. It is preferred that the vials contain 2 ml, 20 ml, 50 ml, 100 ml, 200 ml or 500 ml of vaccine or the combination vaccine.

The invention will now be further explained using the following examples.

EXAMPLES

Example 1: Lung Lesion Score

Challenge Materials:

Bacterin *M. hyopneumoniae*, strain 98, frozen in aliquots of 1 ml and stored at <−50° C. was used.

Preparation of Challenge Materials:

*M. hyopneumoniae* strain 98 was diluted 2000 times in FRIIS+20% SPF serum. This culture was incubated at 37° C. (50 RPM) for four to five days. After four and five days of incubation, samples of this culture were taken for challenge. Viable count was performed before and after challenge by inoculating 4.5 ml FRIIS broth+20% SPF (specific pathogen-free) serum with 0.5 ml culture, mixing and transferring 0.5 ml of culture from one tube to the next, until $10^{-10}$. CCU (color change units) tubes were incubated at 37° C. for three weeks.

Challenge Procedure:

Seventy-two SPF pigs, three weeks (±3 days) of age, were allotted to 6 groups of 12 animals each. Four animals per group were added to groups 1-4 for a total of 16 animals per group. All animals were challenged intra-tracheally using a catheter with 10 ml pure culture on two consecutive days.

Dosage and Administration:

The vaccine contained porous cationic maltodextrin nanoparticles loaded with dipalmitoyl-phosphatidyl glycerol, having a $D_{50}$ value of 37 nm and a zeta potential of +37 mV, at an amount of 2.9 mg particles per dose of 0.4 ml. Test vaccines were made with Mhyo bacterin and Mhyo lysate, the latter type of antigen being typically more effective when used with nanoparticles in the prior art. The bacterin vaccine was prepared by mixing the particles and bacterin formulation (BEI inactivated Mhyo bacteria) at a weight ratio of 1:1 (particles:Mhyo antigen) and leave the mixture for 24 hours to settle to arrive at an association of the particles and antigen. The lysate vaccine was made accordingly, differing in that the bacterin was subjected to a sonication procedure to lyse the cells. The zeta potential of the particles after association with the Mhyo antigen was +14.9 mV for the bacterin vaccine and +15.6 mV for the lysate vaccine.

At three and five weeks of age, piglets were vaccinated locally (intranasally) or systemically (using the IDAL® vaccinator, depositing the vaccine partly in the dermis and partly in the muscular tissue) in the neck according to Table 1. As a positive control the commercial product Porcilis® Mhyo ID ONCE was used according to manufacturer's instructions.

The novel vaccine did not induce unwanted sited effects and was regarded safe. The pigs were euthanized at day 21 post challenge to determine the lung lesion score due to pneumonia. During necropsy the percentage of lung lesions was determined, and the score was transformed into a Goodwin & Whittlestone score (supra) resulting in the lung lesion score. The results are shown in Table 1.

TABLE 1

| | | | Median Lung Legion Score | | | |
|---|---|---|---|---|---|---|
| | Positive control | NP w/o Mhyo antigen | NP + IN bacterin | NP + ID bacterin | NP + IN lysate | NP + ID lysate |
| Median LLS | 1.5 | 8 | 11.5 | 2.5 | 9 | 9 |

*NP = Nanoparticles; IN = intranasal; ID = intradermal; w/o = without

As can be inferred from Table 1, the lung lesion score is significantly lowered for the systemic administration of a vaccine comprising Mhyo bacterin and nanoparticles as compared to the local application. Also, the bacterin vaccine was substantially more effective than the Mhyo lysate. This is surprising over the art wherein the present nanoparticles are typically applied for local vaccination using lysate as antigen.

Example 2: Single Vs Two-Dose Administration

In analogy to Example 1 described above, the LLS was determined for four groups of pigs each containing 20 pigs.

In group 1 (one-shot ID), the pigs were vaccinated intradermally at week 4 with a single dose (one-shot) vaccination of 0.2 mL of vaccine. In group 2 (two-shot ID), the pigs were vaccinated intradermally at week 1 with a prime vaccination of 0.2 mL followed by a boost vaccination with 0.2 mL at week 4. In group 3, the pigs were vaccinated intradermally at week 4 with a single dose (one-shot) of 0.4 mL of vaccine. In group 4, no vaccination took place. The vaccine in groups 1 to 3 was identical and contained nanoparticles and Mhyo bacterin (weight ratio 1:1), wherein each dose of 0.2 ml contained 2.18 mg of nanoparticles. The zeta potential of the formulated particles was +15.2 mV.

The results are shown in Table 2 here below.

TABLE 2

| | | LLS after vaccination | | |
|---|---|---|---|---|
| | One-shot ID (0.2 mL) | Two-shot ID: Each 0.2 mL | One shot ID (0.4 mL) | Negative control (no vaccine) |
| Median LLS | 1.5 | 2.7 | 1.0 | 10.0 |

As can be seen, the single dose administration, quite surprisingly, does not result in an increased LLS over a two-shot administration. Even stronger, the LLS seemed to be further decreased. This means that with the current vaccine a single dose vaccination may be used to arrive at effective protection against Mhyo.

Example 3: Stability of PRRSV Vaccine

In order to determine the stability of live attenuated PRRSV vaccine in the presence and absence of the nanoparticles, PRRSV was mixed in the common vaccine diluent Diluvac Forte® (MSD Animal Health) with and without nanoparticles. The TCID50 (Tissue Culture Infection Dose 50) of PRRSV on MARC cells was determined at 0, 45, 90 and 150 min. The TCID50 corresponds to the effectiveness of the PRRSV antigen. For the experiment, in each case 1.67 mg of the nanoparticles (see Example 1) where added to an eppendorf tube, to which tube a dose of live PRRS virus in diluent was added, aiming at about 7.2*10^5 TCID50 per tube. As can be seen from Table 3 below and the TCID50 value (*10^5) at each measured time interval, the stability of PRRSV was increased in the presence of nanoparticles compared to the formulation without the nanoparticles.

TABLE 3

| | Stability of PRRSV | | | |
|---|---|---|---|---|
| | TCID50 at 0 min | TCID50 at 45 min | TCID50 at 90 min | TCID50 at 150 min |
| Diluent | 6.75 | 5.75 | 5.15 | 3.15 |
| Diluent + NP | 6.75 | 6.35 | 5.55 | 4.75 |

* NP = nanoparticles;
TCID50 = Tissue Culture Infection Dose 50

As can be seen from the results depicted in Table 3, the stability of PRRSV in diluent is surprisingly increased in the presence of the nanoparticles, which means that the effectiveness of the combination vaccine is also increased for the PRRSV component.

The invention claimed is:

1. A vaccine comprising nanoparticles and a *Mycoplasma hyopneumoniae* bacterin, wherein the *Mycoplasma hyopneumoniae* bacterin is associated to the outside of the nanoparticle via non-covalent attachments and wherein nanoparticles comprises a cationic polysaccharide that is a porous polysaccharide and an anionic phospholipid.

2. The vaccine according to claim 1, wherein the anionic phospholipid is selected from diacylphosphatidyl glycerol, diacylphosphatidyl serine and diacylphosphatidyl inositol.

3. The vaccine according to claim 1, wherein the cationic polysaccharide is obtainable by reacting crosslinked maltodextrin with glycidyl-trimethylammonium.

4. The vaccine according to claim 1, further comprising a pharmaceutically acceptable solvent.

5. The vaccine according to claim 1, wherein the vaccine is essentially free of oil and/or aluminium hydroxide and/or saponins and/or carbopol.

6. A method for the prophylaxis of an infection with *Mycoplasma hyopneumoniae* in pigs comprising administering an effective amount of the vaccine according to claim 1.

7. The method according to claim 6, wherein the vaccine is administered systemically.

8. The method according to claim 6, wherein the vaccine is administered intradermally.

9. The method according to claim 6, wherein the vaccine is administered as a single dose.

10. The method according to claim 6, for use in the reduction of lung lesions due to the infection with *Mycoplasma hyopneumoniae.*

11. A kit of parts comprising a first vaccine, a second vaccine and a leaflet, wherein the first vaccine is a vaccine according to claim 1 and the second vaccine comprises live attenuated porcine reproductive and respiratory syndrome virus (PRRSV).

12. A combination vaccine comprising a mixture of a first vaccine and a second vaccine, wherein the first vaccine is a vaccine according to claim 1 and the second vaccine comprises live attenuated porcine reproductive and respiratory syndrome virus (PRRSV).

13. A vial comprising the vaccine according to the combination vaccine of claim 12.

14. A vial comprising the vaccine according to claim 1.

\* \* \* \* \*